(12) United States Patent
Kuwahara et al.

(10) Patent No.: US 6,844,164 B1
(45) Date of Patent: Jan. 18, 2005

(54) ANTIBODY AGAINST RAT POSTACROSOME REACTION SPERM AND UTILIZATION THEREOF

(75) Inventors: Yoshihiro Kuwahara, Osaka (JP); Michinori Hasegawa, Hyogo (JP); Kiyotsugu Isaka, Osaka (JP); Hiromasa Araki, Nara (JP)

(73) Assignee: FUSO Pharmaceutical Industries, Ltd., Osaka (JP)

( * ) Notice: Subject to any disclaimer, the term of this patent is extended or adjusted under 35 U.S.C. 154(b) by 3 days.

(21) Appl. No.: 10/111,569

(22) PCT Filed: Oct. 23, 2000

(86) PCT No.: PCT/JP00/07374
§ 371 (c)(1),
(2), (4) Date: Oct. 9, 2002

(87) PCT Pub. No.: WO01/30853
PCT Pub. Date: May 3, 2001

(30) Foreign Application Priority Data

Oct. 26, 1999 (JP) ............................ 11/304530

(51) Int. Cl.[7] .......................... C07K 16/28; C12N 5/20; G01N 33/543; G01N 33/553; G01N 33/567
(52) U.S. Cl. .......................... 435/7.21; 435/2; 435/7.92; 435/7.94; 435/7.95; 435/70.2; 435/452; 435/332; 435/806; 435/975; 436/503; 436/518; 436/524; 436/526; 436/528; 436/172; 530/388.2; 600/35
(58) Field of Search .......................... 435/2, 7.2, 7.21, 435/7.92, 7.94, 7.95, 70.21, 452, 332, 806, 975; 436/518, 524, 526, 528, 503, 172; 530/388.2; 600/35

(56) References Cited

FOREIGN PATENT DOCUMENTS

| | | |
|---|---|---|
| EP | 387873 A1 | 9/1990 |
| JP | 4-268454 | 9/1992 |
| JP | 06-178634 A | 6/1994 |
| JP | 10-185919 A | 6/1998 |

OTHER PUBLICATIONS

Masaru Okabe, et al, "Capacitation–related changes in antigen distribution on mouse sperm heads and its relation to fertilization rate in vitro", Journal of Reproductive Immunology, vol. 11, No. 2, pp. 91–100,, 1987.

T. Yoshiki, et al, "Molecular nature of sperm acrosomal antigen recognized by HS–13 monocolonal antibody" Journal of Reproductive Immunology, vol. 36, No. 1–2, pp. 61–75, 1997.

R. Jones, et al, "Topographical rearrangement of a plasma membrane antigen during capacitation of rat spermatozoa in vitro", Development Biology, vol. 139, No. 2, pp. 349–362, 1990.

R. Shalgi, et al, "Antigen on rat spermatozoa with a potential role in fertilization" Molecular Reproduction and Development., vol. 25. No. 3, pp. 286–296, 1990.

Lynn Fraser, "$Ca^{2+}$ is required for mouse sperm capcitation and fertilization In vitro" Journal of Andrology, vol. 3, pp. 412–419, Nov./Dec. 1982.

*Primary Examiner*—Christopher L. Chin
*Assistant Examiner*—James L. Grun
(74) *Attorney, Agent, or Firm*—Browdy and Neimark, PLLC (57) ABSTRACT

An antibody biding specifically to rat's acrosome reacted sperm is produced and hybridomas (FARS-91 and FARS-92 strains) capable of stably proliferating are obtained by fusing mouse spleen cells having a high antibody titer against rat's acrosome reacted sperm with mouse-origin myeloma cells and screening fused cells reacting strongly with rat's acrosome reacted sperm. From these hybridomas, monoclonal antibodies selectively binding to rat's acrosome reacted sperm can be obtained. Thus, a diagnostic method for evaluating fertility of rat's spermatozoa is presented.

12 Claims, 10 Drawing Sheets

ANTIBODY AGAINST RAT POSTACROSOME REACTION SPERM AND UTILIZATION THEREOF

This application is a 35 U.S.C. 371 filing of PCT/JP00/07374 filed 23 Oct. 2000.

TECHNICAL FIELD

The present invention relates to monoclonal antibodies selectively binding to rat acrosome reacted sperm, hybridomas producing said monoclonal antibodies, and a method for evaluating fertility of rat spermatozoa using said monoclonal antibodies. The invention also relates to a method for screening materials effecting on rat fertility, characterized in using said method for evaluating fertility.

BACKGROUND ART

It is now obligated to do reproductive and developmental toxicity studies in studies relating to safety of a drug on the occasion of an application of manufacturing approval for the drug. The reproductive and developmental toxicity studies mean that animal experiments are conducted to obtain information on whether the application of a drug to living bodies could possibly induce some adverse effect in the course of reproduction and development. The experimental results can be extrapolated to humans and utilized in the evaluation of safety (risk) of the drug to reproduction and development in humans. A guideline for reproductive and developmental toxicity studies promulgated in 1997 was revised and enacted in conformity with the ICH guideline (International Conference on Harmonization of Technical Requirements for Registration of Pharmaceuticals for Human Use; at the international conference for harmonization of regulation of pharmaceuticals in three areas involving Japan, USA and EU) which was advised on 1994. In this guideline, it is described that histopathological examinations of reproductive organs and a sperm analysis in repeated-dose toxicity studies should be made relative to evaluation of male fertility in studies relating to fertility and early embryonic development to implantation.

To perform the histopathological examination for male reproductive organs, however, skillful technique is required, and there is sometimes a case given an effect to spermatozoa which could not be detected by means of the histopathological examination. In order to correctly evaluate fertility and precisely examine an effect of a drug on spermatozoa, it is necessary to perform the fertility examination of spermatozoa themselves as well as the histopathological examination.

In the current reproductive and developmental toxicity studies, no examination of concentration, motility, morphology of spermatozoa and the like that have been performed in human sperm analysis. Accordingly, an investigation for establishing a method for evaluation of spermatozoa motility is now being continued. This means that a method for evaluation of fertility has not yet been established.

As for examinations of fertility of human spermatozoa, a hamster test, conserved zona pellucida passage test, and triple-stain test and the like have been developed. The hamster test is a method for evaluating fertility, in which the properties of spermatozoa are utilized, that is, only spermatozoa which have the capacitation and in which the acrosome reaction have been completed, can enter the zona-free hamster eggs. The conserved zona pellucida passage test is a method in which the properties of spermatozoa are utilized, that is, only spermatozoa which have the capacitation, in which the acrosome reaction have been completed and in which the motility is retained sufficiently, can pass through the conserved pellucid zone.

The triple-stain method is a method for distinguishing dead spermatozoa, live spermatozoa and spermatozoa of intact acrosome by means of staining them with a combination of three types of staining methods.

When the above-mentioned test that, so far, is known for human spermatozoa is applied to the reproductive and developmental toxicity studies, it is necessary to collect eggs to eliminate the zona pellucida, or to permits maturation of the collected immature eggs in vitro and preserve them in a particular salt solution at a high concentration to form the zona pellucida. These procedures, however, require skillful technique and troublesome operation as well as expensive equipment. When the influence of chemical materials such as drugs or environmental hormones on fertility of spermatozoa is examined, in the current reproductive and developmental toxicity studies the decision whether or not to be fertilized on an experimental animal is not determined from their appearance as long as the fetus has grown up to some degree after mating. This necessitates time and cost. Even though many points such as the number of spermatozoon, mobility and morphology, which appear to have some influence on fertilization, are examined, it is impossible to determine the exact fertility so long as the presence of acrosome reaction as an essential factor for fertilization cannot be confirmed.

DISCLOSURE OF INVENTION (Problems that the Invention is to Solve)

It is now necessitated, in the current reproductive and developmental toxicity studies, to develop an accurate and conveniently operable method for evaluating fertility of spermatozoa, in which the test can be completed within a short period of time. It is also necessary that the test results in the above method can be extrapolated to humans.

(Means for Solving the Problems)

The present inventors paid attention to utilizing an antigen-antibody reaction in order to solve the above problems.

The present inventors have succeeded in preparing monoclonal antibodies specific to non-human animal spermatozoa post acrosome reaction as well as hybridoma producing said monoclonal antibodies. At the same time, using these monoclonal antibodies, they established a method for evaluating fertility of spermatozoa, wherein the test results can be extrapolated to humans, and they also prepared a composition for use in determining fertility. Moreover, they also established a method for screening materials that affect fertility.

According to the invention, it is possible to complete the tests within a short period of time and to evaluate the fertility of spermatozoa accurately in a convenient operation.

The principle for evaluating fertility in the invention is as follows. The spermatozoa just after ejaculation in mammals have no ability to fuse (fertilize) an egg. First, adsorptive materials such as glycoproteins and glycolipids contained in epididymis secretion or seminal fluid, which cover the surface of the protoplasmic membrane of the spermatozoa to protect the spermatozoa in female reproductive organs, are removed or denatured. This physiological alteration is called "capacitation". Subsequently, the spermatozoa reaching the ampulla of tubue uterinae, which is a spot for fertilization, make an approach to an egg and cause an "acrosome reaction". The acrosome reaction means a phenomenon in which the outermost protoplasmic membrane of spermatozoa fuses to the acrosomal outer membrane enveloping the outside of the acrosome to open a small pore, through which an acrosomal enzyme is released from the acrosome. Only the spermatozoa that have caused the acrosome reaction can fuse to the egg (fertilization) through dissolution of the oval ambient pellucid zone by the acrosomal enzyme. Accordingly, the occurrence of the acrosome reaction is an essential condition for fertilization, and confirmation of the occurrence of the acrosome reaction is a direct method for evaluating fertility of spermatozoa. The method of the invention, accordingly, can be used in evaluating the fertility of spermatozoa conducted in rats for the purpose of the reproductive and developmental toxicity studies and the like, on the assumption that the obtained test results can be extrapolated to humans.

In this connection, in order to carry out the evaluation of fertility used in extrapolation to humans, it is necessary to choose experimental animals whose physiological state is very similar to that of humans. Until now, monoclonal antibodies to non-human animal acrosome reacted sperm have been reported on mice (Masaru Okabe et al., Journal of Reproductive Immunology, 11(2), 91–100, 1987), although as experimental animals used in extrapolation to humans, rats whose general metabolic pathways are well known have widely been used.

Therefore, monoclonal antibodies by which the occurrence of the acrosome reaction of rat spermatozoa can be distinguished were produced using rats, an animal species which is the most studied in experimental reproduction and development and whose physiological state is very similar to that of humans.

At present, regarding pharmaceuticals inhibiting the acrosome reaction of human spermatozoa, bicuculline (Calogero A. E. et al; Fertility and Sterility, 71(5), 930–936, 1999), wortmannin (Fisher H. M. et al; Molecular Human Reproduction, 4(9), 849–855, 1998), cysteamine (Sengoku K. et al; Journal of Andrology, 19(1), 37–49, 1998), anantin (Rotem R. et al; American Journal of Physiology, 274(2 Pt 1), E218–223, 1998), chlordane and endosulfan (Turner K. O. et al; Journal of Andrology, 18(6), 571–575, 1997), etc., have been reported. In the future, monoclonal antibodies to acrosome reacted sperm will be useful for investigating the effect of drugs on the acrosome reaction of spermatozoa in the reproductive and developmental toxicity studies.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIGS. 1A and B show the same field of vision.

FIG. 2 is a photomicrograph showing reactivity of the antibody FARS-91 to acrosome reacted sperm (spermatozoa treated with A23187).

FIGS. 2A and B show the same field of vision.

FIG. 3 is a photomicrograph showing reactivity of the antibody FARS-92 to acrosome reacted sperm (spermatozoa as control treated with A23187).

FIGS. 3A and B show the same field of vision.

FIG. 4 is a photomicrograph showing reactivity of the antibody FARS-92 to acrosome reacted sperm (spermatozoa treated with A23187)

FIGS. 4A and B show the same field of vision.

FIG. 5 is a photomicrograph showing the frozen and thawed spermatozoa observed by FITC-PSA staining.

FIG. 6 is a photomicrograph showing reactivity of the antibody FARS-91 with the frozen and thawed spermatozoa.

FIG. 7 is a photomicrograph showing reactivity of the antibody FARS-92 with the frozen and thawed spermatozoa.

FIG. 8 is a photomicrograph showing reactivity of the antibody FARS-91 with the frozen and thawed spermatozoa after treatment with A23187.

FIGS. 8A and B show the same field of vision.

FIG. 9 is a photomicrograph showing reactivity of the antibody FARS-92 with the frozen and thawed spermatozoa after treatment with A23187.

FIGS. 9A and B show the same field of vision.

FIG. 10 is a photomicrograph showing reactivity of the antibodies FARS-91 and FARS-92 with the frozen and thawed human spermatozoa.

BEST MODE FOR CARRYING OUT THE INVENTION

According to the invention, monoclonal antibodies to rat acrosome reacted sperm and two hybridomas, FARS-91 and FARS-92, producing said antibodies were obtained. These hybridomas were deposited respectively in the Ministry of International Trade and Industry, National Institute of Bioscience and Human-Technology (NIBH), located in 1—1-3, Higashi, Tsukuba-shi, Ibaragi, 305-8566, Japan, respectively, as accession nos. FERM BP-7401 and FERM BP-7402, on Oct. 13, 1999.

In producing the above antibodies, first, fresh rat spermatozoa, which are collected by ejaculation or by removal of the cauda epididymis or seminal duct and which have not led to acrosome reaction (hereinafter referred to as fresh rat spermatozoa), are provided and the acrosome reaction induced. Next, the rat acrosome reacted sperm serving as antigens are used to immunize mammals. Rat acrosome reacted sperm may be prepared by inducing the acrosome reaction by a chemical procedure, by inducing a pseudo acrosome reaction, by induction of the acrosome reaction in culture, or by a combination of these procedures and the like.

The fresh spermatozoa may be obtained, for example, from the extirpated cauda epididymis or seminal ducts. When the spermatozoa are collected from the cauda epididymis, said cauda epididymis is cleaved into 3 or 4 parts. When the seminal ducts are used, one duct is cut into 3 to 5 portions. These are then immersed and gently swirled in a culture medium such as TYH medium containing 0.4% BSA or m-KRB medium containing 0.5% BSA, at 30–40° C., for example, for 10 minutes, until the spermatozoa migrate. Alternatively, when collected from the cauda epididymis, the spermatozoa may be obtained by cutting a part of the seminiferous tubule removed from the cauda epididymis and scooping it up with a round-pointed Pasteur pipette.

The chemical induction of the acrosome reaction is exemplified by a method for treating fresh rat spermatozoa with a calcium ionophore such as A23187. In addition, a method for treating with an anionic surfactant, e.g., sodium deoxycholate, or a cationic, non-ionic or ampholytic surfactant, may be employed.

The induction of a pseudo acrosome reaction may be achieved, for example, by physically destroying the acrosomal outer membrane to expose the acrosomal intima. Herein, this type of acrosome reaction is referred to as a "pseudo acrosome reaction". The pseudo acrosome reaction may be carried out, for example, by freezing fresh rat spermatozoa at around −20° C. and then thawing. Alternatively, electroporation or ultra-sonication may be utilized.

In a method for inducing acrosome reaction in culture, the method in which fresh rat spermatozoa are cultured in a medium containing calcium is exemplified. The concentration of calcium in the culture medium is preferably set in a range of 0.5–5 mM, particularly at 1.8 mM. As a source of calcium, calcium chloride, calcium nitrate, calcium lactate, calcium gluconate, or the like may be used. As for the culture medium to be used, media such as m-KRB, M-199, TYH and the like are included. The TYH medium is composed of 6.976 g/L of sodium chloride, 0.356 g/L of potassium chloride, 0.251 g/L of calcium chloride dihydrate, 0.293 g/L of magnesium sulfate heptahydrate, 0.162 g/L of potassium hydrogen phosphate, 2.160 g/L of sodium hydrogen carbonate, 0.111 g/L of sodium pyruvate, 1.000 g/L of glucose, 4.0 g/L of bovine serum albumin, and 4.8 mL of 50% syrup of sodium lactate. Additionally, an antibiotic or anti-fungal agent, e.g., penicillin, streptomycin, amphotericin B, etc, may be added to the medium.

Moreover, the above-mentioned methods for inducing acrosome reaction may be used in combination. For example, a method comprising treatment with A23187 followed by freezing and thawing may be employed. Alternatively, fresh spermatozoa may be cultured in a medium containing calcium, during which A23187 is also added. In such a case, the concentration of A23187 is preferably added alone at a oncentration lower than that for inducing the acrosome reaction.

Immunization may be performed on a mammal such as mouse, rat, and the like. As a mammal, it is desirable to use an inbred animal strain with permanently growing cells, which are used as a partner in cell fusion. Both of male and female animals may be used, preferably at the age of, for example, 3–10 weeks old. The number of rat spermatozoa used in immunization, for example, for one mouse, is preferably $1 \times 10^3$–$1 \times 10^{10}$. The spermatozoa are preferably mixed with, for example, Freund's complete adjuvant, Freund's incomplete adjuvant, aluminum adjuvant, pertussis adjuvant, endotoxins of gram-negative bacteria (*Escherichia coli, Salmonella*, etc.), alum precipitate, clay grains (bentonite), aluminum compounds, oils, vitamins, plant polysaccharides, and the like to form an emulsion, which is then administered to animals intraperitoneally, intravenously, subcutaneously, or intracutaneously. The immunization may be done 1 to 5 times at intervals of 1–3 weeks. In the immunized animals, polyclonal antibodies to rat acrosome reacted sperm can be obtained from their body fluid or antibody-producing cells contained in the body fluid. When the antibody titer has increased sufficiently by measurement of the antibody titer of the animals, the antibodies or antibody-producing cells are collected.

In order to obtain monoclonal antibodies to rat acrosome reacted sperm, it is necessary to make hybridomas by fusing the antibody-producing cell with a permanently growing cell. Preparation of hybridomas may be carried out as follows below.

The antibody-producing cells can be obtained from spleen, lymph node, peripheral blood, etc., with the spleen being preferred. The spleen of the immunized mammal is extirpated aseptically 2–5 days after the final immunization to make a suspension of spleen cells. As the permanently growing cells for use as partners for fusion, cells which have been known by the person skilled in the art and which have a permanently growing property can optionally be used, even though myeloma cells have widely been used. It is preferable to use the permanently growing cells derived from an animal homologous to that from which the antibody-producing cells have been obtained. In the case of mice, P3U1P3X63-Ag8.U1 (P3U1), P3/NS1/1-Ag4-1 (NS-1), SP2/0-Ag14 (SP-2), P3X63Ag8 (X63), P3X63-Ag8.653 (653), and the like may be used. As for the permanently growing cells, it is preferable to use those having a characteristic property utilizable as a marker in selection, for example, 8-azaguanine resistant cell line, hypoxanthine guanine phosphoribosyl transferase-lacking cell line, etc. These cell lines can be obtained from the American Type Culture Collection (ATCC).

For fusion, any one of these permanently growing cells is cultured in a growth medium, then washed with, for example, a DMEM medium, and collected by centrifugation prior to fusion. Fusion is achieved by mixing an antibody-producing cell with the permanently growing cell in a culture medium such as MEM, DMEM or RPMI1640, to which is added a cell-fusing agent such as polyethylene glycol. If required, a small quantity of dimethylsulfoxide may be added in order to accelerate the cell fusion. The resulting hybridoma is cultured in a FCS-containing MEM or RPMI1640 medium containing hypoxanthine, aminopterin, thymidine, etc. After a duration of about 1 week, the culture medium is changed to an FCS-containing MEM or RPMI1640 medium containing hypoxanthine and thymidine.

The hybridoma is then subjected to screening and cloning. In screening, the supernatant of hybridoma culture is collected and screened by a known labeled antibody method, for example, radioimmunoassay, enzyme antibody method, fluorescent antibody method, etc., using rat acrosome reacted sperm as antigen. Subsequently, a population of hybridomas producing a single monoclonal antibody is selected with cloning by a known technique such as, for example, limiting dilution or soft agar method. It is preferred that screening and cloning be repeated two times or more.

The hybridoma obtained as described above may be cultured in vitro (in a culture vessel or in a nutrition medium) or in vivo (in the living body or in animal tissue) to produce a monoclonal antibody. When cultured in vitro, the hybridoma is cultured in a suitable medium such as FCS-containing MEM medium, RPMI1640 medium, etc., and the desired monoclonal antibody can be obtained from the supernatant of the culture. When cultured in vivo, the respective hybridomas are transplanted in the abdominal cavity of an animal that has a homologous histocompatibility to an animal from which the permanently growing cell is derived, and are proliferated. Alternatively, the respective hybridomas are transplanted in nude mice, and the monoclonal antibodies produced in the ascites may be collected. Prior to transplantation of the hybridoma, it is preferred to administer intraperitoneally a mineral oil such as 2, 6, 10, 14-tetra-methylpentadecane (pristane).

The monoclonal antibodies contained in the culture supernatant or in the supernatant of the ascites may be conventionally purified as known to a person skilled in the art, although the antibodies can be used without purification depending on the purpose. The purification may be achieved, for example, by means of salting out, such as by ammonium sulfate precipitation, gel filtration with Sephadex, etc., dialysis with 0.02M phosphate buffer (pH 7.2), etc., ion-exchange chromatography, electrophoresis, ultrafiltration, affinity chromatography, high performance liquid chromatography, and the like.

In an embodiment of the invention, the antibodies of the invention can be used in immunoassays such as immune staining, immune precipitation, immunoblotting, etc., for example, competitive or non-competitive immunoassay, radioimmunoassay, ELISA, latex aggregation, affinity column, and the like. When ELISA is employed, a sandwich assay is preferred. The immunoassay herein includes all methods utilizing immune reaction such as immunohistological examination, immunoblotting, immune precipitation, and the like. The antibodies of the invention can be used in the collection and purification of rat acrosome reacted sperm since they can be utilized in the above-mentioned methods.

The antibodies of the invention can be used, for example, in evaluating the fertility of rat spermatozoa in the reproductive and developmental toxicity studies that relate to a safety study. In this method, spermatozoa to be evaluated are allowed to contact a labeled antibody of the invention, and the label attached to the spermatozoa is detected by a way of label detection. Alternatively, the spermatozoa are allowed to contact an unlabeled antibody of the invention, which is then allowed to contact a labeled second antibody (antibody capable of binding to the antibody of the invention). Thus, the label attached to the spermatozoa is detected by means of label detection.

Labeling of antibodies may be effected, for example, with a fluorescent material such as FITC (fluorescein isothiocyanate) and RITC (tetramethylrhodamine isothiocyanate), a radioactive material such as radioactive iodine, radiocarbon, tritium, radium, strontium, etc., an enzyme such as peroxidase, an enzyme substrate, a coenzyme, an enzyme precursor, an apoenzyme, a pigment, a chemiluminescent compound, a luminescent material, a color-producing material, a magnetic material, metal particles, and the like. Production of the second antibodies and attachment of a label to the antibodies may be achieved by a conventional means known to a person skilled in the art. A method for determining a fluorescent material includes, for example, a method of observing fluorescence excitation with ultraviolet rays under a fluorescence microscope, a method of quantitatively determining fluorescence intensity under irradiation of a certain excitation light, or the like. As a method for measuring radioactive materials, for example, the amount of radiation can be measured using an α-ray spectrometer, a scintillation counter, an ionization box, a counter, etc., to determine the rat acrosome reacted sperm. As a method for measuring an activity of peroxidase, for example, color development is conducted with o-phenylenediamine as a substrate, where the optical density is measured to determine the rat acrosome reacted sperm.

As for a composition for measuring fertility using an antibody of the invention, a composition in which the present antibody is kept, for example, on beads (granules), is available. The beads on which the antibody is kept include carriers such as glass, Agarose, Sepharose, Agarose-loaded porous diatomaceous earth, hydrophilic copolymeric acryl gel, polystyrene, and the like. Preferably, superparamagnetic carriers in which a magnetizable material (e.g., $Fe_2O_3$) is contained in the core are used. The shape of the granules is optional, including spherical form, amorphous fractured form, etc., with a spherical form being preferred. There is no limitation in particle size, which may be, for example, in a range of several micrometers to several hundred micrometers.

Alternatively, it is also possible to examine fertility of rat spermatozoa, for example, by observing aggregation formed by the binding of the spermatozoa to the above-mentioned antibody-carrying beads. Theoretically, the beads are cocultured with a certain number of fresh spermatozoa in wells on a microplate for a certain period of time. After incubation of a certain period, the acrosome reaction starts to occur and binding of spermatozoa and beads is induced due to an antigen-antibody reaction. Further incubation leads to an increase in the number of spermatozoa bound to beads due to an increase in the number of spermatozoa after induction of the acrosome reaction. The beads aggregate due to the motion of the bound spermatozoa. When a certain number of spermatozoa is cocultured together with a certain number of beads, the ability to induce the acrosome reaction can be estimated from the amount of spermatozoa bound to the beads. Though the state of binding of spermatozoa to beads may be observed at any time, it may be effected twice, 1–2 hours after incubation and 6–8 hours after incubation. Thus, the rate of induction of the acrosome reaction can be decided from the value after 1–2 hours. The cumulative number of spermatozoa in which the acrosome reaction has occurred can be decided from the value after 6–8 hours. In this state, when spermatozoa having fertility are present at a certain number or more, multivalent binding between granules and spermatozoa is induced and granules soon start to form aggregates, and granules or granule mass having no spermatozoa binding may disappear. Thus, it is possible to find the rate of spermatozoa having fertility by examining the spermatozoa concentration at which a certain number of beads can form aggregate.

Alternatively, the complex of spermatozoa and the above antibody-carrying beads (beads carrying a primary antibody) is gathered with a magnet in order to wash the complex, and then a secondary antibody labeled with a fluorescent compound is added to determine the number of rat acrosome reacted sperm. The secondary antibodies may be those which recognize rat spermatozoa or rat spermatozoa after the acrosome reaction.

When the secondary antibody recognizes rat acrosome reacted sperm, it is desired that the epitope recognized by the secondary antibody is different from that recognized by the primary one.

In order to practice the above test, it is convenient to make a kit comprising materials necessary for carrying out the test. Such a kit may contain granules for test, a plate having wells, a culture medium for incubating sepermatozoa and the like. The culture medium may contain mineral salts, organic acid salts, sugars, serum albumin, antibiotics, indicators, and the like. In addition, the kit may contain test tubes, tubes for centrifugation, other similar glass vessels, pipettes or similar suction instruments, a microscope, and the like. In place of the above granules for test, a kit may be included a good combination of the antibodies and the solid granules as raw material.

The plate equipped with wells for use in the invention may be made of plastic, ceramics, glass, enamel, and the like. The bottom of the well may be in any shape such as flat, U- or V-shape, with a flat bottom being preferred. The vertical section of the well is usually in a circular form. The number of the wells present on a plate, for example, 96 wells, is optional. Observation is usually carried out under a microscope, preferably at a magnification of 100–400.

More specifically, for example, a TYH culture broth containing no sodium hydrogen carbonate and bovine serum albumin, 2–15% sodium hydrogen carbonate aqueous solution, lyophilized bovine serum albumin, FARS-91 or FARS-92 antibody-binding beads, and 20–70% glycerin solution are used. First, 1 mL of 7% sodium hydrogen carbonate solution is preferably added to 22 mL of TYH culture broth and mixed. Thereafter, lyophilized bovine serum albumin is added thereto and dissolved without forming foam to prepare 0.4% bovine serum albumin-containing TYH culture broth. A vial containing the culture broth, of which the mouth was capped with a flame-sterilized aluminum foil, was equilibrated in a 5% carbon dioxide gas incubator at 37° C. for 1–18 hours, and may be used in a test. In addition, FARS-91 antibody or FARS-92 antibody-binding beads are mixed well in a test tube mixer for about 30 seconds, of which 20 $\mu$L is immediately distributed into 0.5 mL sterilized microtube, and 380 $\mu$L of the culture broth is then accurately added to the microtube. At this time, the concentration of the beads may be adjusted to $1.0 \times 10^3$–$1.0 \times 10^3 10$ particles/mL, preferably, $0.5 \times 10^6$ particles/mL (bead suspension). After adjustment, the mixture is preferably preserved in a cold environment. 50% Glycerin solution may be added to a spermatozoa suspension in an amount equal to that of the spermatozoa suspension at the time of counting spermatozoa in order to ease the counting.

Next, a test tube containing the culture broth is provided, to which is added fresh rat spermatozoa. The mixture is then gently dispersed for several minutes, and the spermatozoa concentration is measured. It is preferable to prepare a spermatozoa suspension at a concentration in which the spermatozoa number is $1 \times 10^6$ particles/mL, using the culture broth. At this time, 50% glycerin solution may be added to a spermatozoa suspension in order to ease the counting.

Next, a sterilized 96-well microplate is provided. The test can be achieved using 4 wells of the plate. That is, 100 $\mu$L of the culture broth is added to the 2nd, 3rd and 4th wells, and the prepared spermatozoa suspension is added to the 1st and 2nd wells. The 2nd well is agitated by means of pipetting, in which 100 $\mu$L is added to the 3rd well. This same operation is repeated to the 4th well, from which 100 $\mu$L is removed. By means of this operation, 1-, 2-, 4 and 8-fold serial dilution can be made for the spermatozoa suspension. The 1st well corresponds to a 1-fold dilution, the 2nd to a 2-fold dilution, the 3rd to a 4-fold dilution, and the 4th to a 8-fold dilution. The bead suspension is suspended on a mixer, in which 100 $\mu$L of each dilution is added to each well. Immediately, each well is gently agitated with the tip of pipette in sequence from the 4th well to the 1st well. The mixture is then incubated without agitation at 37° C. in 5% carbon dioxide gas. Then, the aggregate formed in the well is observed in order to determine fertility.

ELISA (double layer method) may be carried out, for example, as follows. For example, rat spermatozoa which have been incubated for a period of time sufficient to induce acrosome reaction are immobilized at the bottom of a well of a plastic plate, to which an antibody (primary antibody) specific to the rat's acrosome reacted sperm is subsequently added. Immobilization of the spermatozoa to be tested in the well may be achieved, for example, by immobilization with paraformaldehyde, etc., and subsequently drying, for example, at 37° C. for about 24 hours. If there are rat spermatozoa in which the acrosome reaction has occurred, an antibody will bind to them. Subsequently, after the wells are washed, for example, an enzyme-labeled second antibody is added to bind to the primary antibody. This enzyme is allowed to react with a coloring substrate, and the absorbance is measured to determine the number of rat acrosome reacted sperm.

ELISA (sandwich method) may be carried out, for example, as follows. An antibody (primary antibody) specific to the rat acrosome reacted sperm is immobilized at the bottom of a well of a plastic plate, to which rat spermatozoa that have been incubated for a period of time sufficient to induce the acrosome reaction are added. If there are rat spermatozoa in which the acrosome reaction has occurred, an antibody will bind to them. Subsequently, after the wells are washed, for example, a fluorescently-labeled second antibody is added to bind to rat acrosome reacted sperm. The fluorescence intensity for this fluorescent substance is measured to determine the number of rat acrosome reacted sperm. In this connection, the primary antibody and the second antibody may be used in a combination with either a monoclonal antibody or a polyclonal antibody. However, in a combination of a monoclonal antibody and another monoclonal antibody, it is preferable that the epitope of each antibody is different from each other.

As a fluorescent antibody technique, for example, a method for directly labeling an antibody to rat acrosome reacted sperm with a fluorescent substance (direct method), a method for labeling an antibody (second antibody) recognizing the antibody to rat acrosome reacted sperm (indirect method), and a method for binding a second fluorescently labeled antibody through a complement, are included.

In a specific example of the indirect method, fresh rat spermatozoa are diluted with 0.1%–5.0%, preferably 0.4%–2.0% BSA-containing TYH culture broth to prepare a mixture at a concentration of $1.0 \times 10^3$ sperms/mL–$1.0 \times 10^{10}$ sperms/mL, preferably $0.2 \times 10^6$ sperms/mL–$1.5 \times 10^6$ sperms/mL. Next, the mixture is incubated for a period of time sufficient for inducing the acrosome reaction, then an antibody to rat acrosome reacted sperm is added, and allowed to react at 30–40° C. for 5–60 minutes. The reaction mixture is washed with the culture broth by centrifugation, an FITC-labeled anti-mouse IgG is added, and allowed to react at 30–40° C. for 5–60, minutes. After the reaction is complete, the mixture is washed several times with 0.001–0.5% $NaN_3$-containing PBS (Ca, Mg free) by centrifugation, and observed under a fluorescence microscope. Thus, the rate of spermatozoa for which fluorescence is recognized at the head can be determined.

Rat spermatozoa used as specimen may be in a state of seminal fluid without processing such as by purification or may be in a state of live spermatozoa isolated by swimming-up, or in a state in which the reactivity with an antibody induced by addition of an agent such as protease to seminal fluid (spermatozoa). The specimen may be in a state of suspension in the culture broth, or in a state of being fixed or immobilized in a plate or dish made of glass or plastic, or in a state of fixation with paraformaldehyde. Fixation with para-formaldehyde may preferably be carried out at a concentration of 0.5–15, preferably 3%–10%.

This antibody can be used in an in vivo screening test of substances that possibly influence the fertility of rat spermatozoa, such as for example, drugs, environmental hormones, etc. The screening test may be carried out, for example, as follows. For example, a substance to be tested is administered, e.g., orally, intravenously, intraarterially, subcutaneously, intramuscularly, intraperitoneally or applied locally (to skin, as eye drops or ear drops, nebula, suppositories, etc.) to a matured week old male rat once a day for a sufficient period required for the whole process of spermatogenesis and maturation of spermatozoa. Then, the spermatozoa are collected, for example, from the cauda epididymis. The collected spermatozoa are incubated, for example, for a sufficient period required for the acrosome reaction, and their fertility is determined by an indirect fluorescent antibody method.

This antibody can also be used in an in vitro screening test of substances possibly influencing the fertility of rat spermatozoa. The screening test may be carried out, for example, as follows. For example, a substance to be tested such as a drug is added to the spermatozoa collected, for example from the cauda epididymis on a fully matured week old male rat, and incubated. Then, after incubation for several minutes to several hours, for example, the fertility is determined by an indirect fluorescent antibody method.

EXAMPLES

The following examples serve to illustrate the invention for further understanding, but they should not be interpreted to limit the technical scope of the invention.

Example 1

Method for Collecting Immunogens

Wistar male rats (age in 14 weeks) were killed by exsanguination under anesthesia with ether, from which the cauda epididymides were removed and immediately placed in a Petri dish containing 10 mL of m-KRB (modified Krebs-Ringer bicarbonate medium) containing 1% BSA (bovine serum albumin; Bayer) warmed at 37° C. (1 plate per cauda epididymis). Cleavages were made at 2–3 parts of the cauda epididymis, which was gently stirred and allowed to stand for about 5 minutes to release spermatozoa. The spermatozoa suspension is moved into a 50 mL tube, into which a calcium ionophore A23187 (Sigma) was added thereto at a final concentration of 10 μM and incubated for about 15 hours in a $CO_2$ incubator. After terminating incubation, the treated spermatozoa were washed twice with PBS(−), then adjusted at a predetermined concentration, and preserved at −20° C.

Example 2

Immunization of Mice

In Jcl female mice (age in 6 weeks), the first day of immunization was regarded as 0 day, and booster immunization was made on the 14th, 21st and 28th days. For immunization, the above-treated rat spermatozoa were administered subcutaneously in the back of the mice at a dose of about $1 \times 10^7$ per shot as an equal mixture with Freund's complete adjuvant and as an equal mixture with Freund's incomplete adjuvant, respectively, on day 0 and on the 14th day. On the 21st and 28th days, only spermatozoa were administered intraperitoneally.

Example 3

Method for Preparation of Hybridoma

Three days after the final immunization, the spleen was removed from the immunized mice and used in cell fusion.

A suspension of splenic cells prepared on an RPMI1640 medium (GIBCO) was mixed with SP-2 cells (murine myeloma cells) at a ratio of about 4:1, permitted to undergo cell-fusion using polyethylene glycol 2000 (Sigma) and then washed with an RPMI1640 medium. Thereafter, the number of cells was adjusted to be about $2 \times 10^6$ cells/mL by dilution with an RPMI1640 medium containing 15% FCS (fetal calf serum; Mitsubishi Chemical), of which 100 μL each was distributed into each well of 96-well microplates, with 6 plates per mouse. The next day, 100 μL of HAT medium (hypoxanthine, aminopterin, thymidine, 15% FCS-containing RPMI1640 medium) was added to each well. On the 2nd, 3rd, 5th and 8th days, half of the medium was replaced with a HAT medium, and on the 10th and 13th days, half of the medium was replaced with an HT medium (hypoxanthine, thymidine, 15% FCS-containing RPMI1640 medium).

Example 4

Screening by ELISA

After treatment with A23187, the frozen-thawed spermatozoa were prepared to $1 \times 10^6$ cells/mL, of which 50 μL each was distributed into each well of a 96-well flat-bottom microplate and dried at 37° C. for about 24 hours for immobilization of the spermatozoa. After immobilization, the plate was blocked with 250 μL of 2% BSA-containing PBS(−), sealed and preserved at 4° C. before use. The plate was used within 5 days after preparation.

The blocking solution in sperm-immobilized plates was washed out, and 50 μL each of the supernatant taken from each well of negative control (20-fold diluted normal murine serum) and positive control (1000-fold diluted spermatozoa-immunized murine serum) as well as 50 µL of the supernatant of cell culture taken from each well 13 days after incubation was distributed in each well and allowed to react at 37° C. for 2 hours. After the reaction was complete, the plates were washed twice with 0.05% Tween 20-containing PBS(-), 50 µL/well of peroxidase-labeled anti-mouse IgG (TAGO), which was one hundred thousand fold-diluted, was added, and allowed to react at room temperature for 2 hours. The plates were then washed in the same manner, 100 µL/well of a substrate solution (60 mg/dL of o-phenylenediamine solution, with 0.006% $H_2O_2$ added) was added, and allowed to react under shading at 37° C. for about 20 minutes. Thereafter, the reaction was terminated with addition of 0.5M sulfuric acid (50 µL/well), and absorbance was measured with a microplate reader (490 nm–650 nm). The specimen exhibiting the absorbance equal to or over that of the positive control was judged to be positive.

Example 5

Screening by an Indirect Fluorescent Antibody Method

After treatment with A23187, the frozen-thawed spermatozoa were prepared to 1×10⁶ cells/mL, where, to 20 µL of the cell suspension 50 µL each of negative control (20-fold diluted normal murine serum) and positive control (1000-fold diluted spermatozoa-immunized murine serum) as well as 50 µL of the cell culture supernatant taken from each well which was positive in screening by the above ELISAs on the 14th day after incubation. The mixture was gently stirred and allowed to react at 4° C. overnight or at 37° C. for 2 hours. After the reaction was complete, the mixture was washed twice with 0.02% $NaN_3$-containing PBS(-), and 20 µL of 400-fold diluted FITC-labeled anti-mouse IgG was added, gently stirred, and allowed to react at 37° C. for 1 hour. After the reaction was complete, the mixture was washed in the same manner, and observed under a fluorescence microscope. The presence of fluorescence recognized at the head of spermatozoon was judged to be positive.

Example 6

Cloning of Fused Cells

Cloning was performed by means of limiting dilution.

The cells of the positive wells were prepared to a cell concentration of 5–100 cells/mL with a cloning medium (HT medium containing 10% brei clone®), of which 100 µL each was distributed to each well of a 96-well microplate. The cloning medium (100 µL) was then immediately added to each well.

For the cells after cloning, the culture medium was changed at a rate of 2–3 times per week (half was replaced with a fresh cloning medium), and screening was performed in conformity with the growth of the cells. Repetition of screening and cloning established hybridomas FARS-91 and FARS-92.

Hereinafter, a monoclonal antibody produced by a mouse—mouse fused cell FARS-91 is referred to as FARS-91 antibody, and a monoclonal antibody produced by a mouse—mouse fused cell FARS-92 as FARS-92 antibody.

Example 7

Determination of Subclass of FARS-91 and FARS-92 Antibodies

Using a mouse monoclonal antibody isotyping kit (Amersham), the sub-class of antibodies was identified.

Three mL of ascites fluid containing FARS-91 antibody or FARS-92 antibody was allowed to react with a typing stick at room temperature for 15 minutes, and then the typing stick was washed 3 times with 5 mL of Tris buffer saline. 3 mL of peroxidase-labeled anti-mouse antibody was then added, allowed to react at room temperature for 15 minutes, and washed in the same manner. Afterwards, 3 mL of a substrate solution was added, allowed to react at room temperature for 15 minutes, and the typing stick was washed 3 times with distilled water. After drying, the sub-class of the antibody was identified by a sign observed on the stick.

As results, it was confirmed that the sub-class of the FARS-91 antibody is IgG, and that of the FARS-92 antibody is $IgG_{2b}$.

Example 8

Reactivity of FARS-91 and FARS-92 Antibodies to Acrosome Reacted Sperm

As described above, fertility of spermatozoa can be determined by confirming whether the acrosome reaction has occurred in the spermatozoa. Accordingly, it was examined whether the monoclonal antibodies obtained in Example 6 can be utilized in the above-mentioned confirmation test.

It has been reported that treating fresh spermatozoa with a calcium ionophore A23187 causes an acrosome reaction in mice (Lynn R. Fraser; Journal of Andrology, 3, 412–419, 1982) and humans (Green et al.; Journal of Cell Science, 32, 321, 1978).

Therefore, the reactivity of FARS-91 antibody and FARS-92 antibody to spermatozoa treated with A23187 (acrosome reacted sperm) and to fresh spermatozoa in rats was examined by an indirect fluorescent antibody method.

Spermatozoa collected from the cauda epididymis of Jcl:SD male rats were prepared to 1×10⁶/mL with 0.4% BSA-containing TYH culture broth. A23187 dissolved in DMSO was added to a final concentration of 2 µM, and the mixture was allowed to react at 37° C. for 20 minutes. As a control, DMSO used as a solvent for A23187 was added and allowed to react in the same manner. After the reaction was complete, the ascites fluid containing FARS-91 antibody or FARS-92 antibody was added, and allowed to react at 37° C. for 30 minutes. The mixture was washed twice with 0.4% BSA-containing TYH culture broth by centrifugation (37° C., 2800 rpm, 5 min), FITC-labeled anti-mouse IgG was added, and allowed to react at 37° C. for 60 minutes. After the reaction was complete, the mixture was washed twice with 0.02% $NaN_3$-containing PBS(-) by centrifugation (room temperature, 2800 rpm, 5 min), and observed under a fluorescence microscope to measure the rate of spermatozoa exhibiting fluorescence on their head.

Figure 1A:
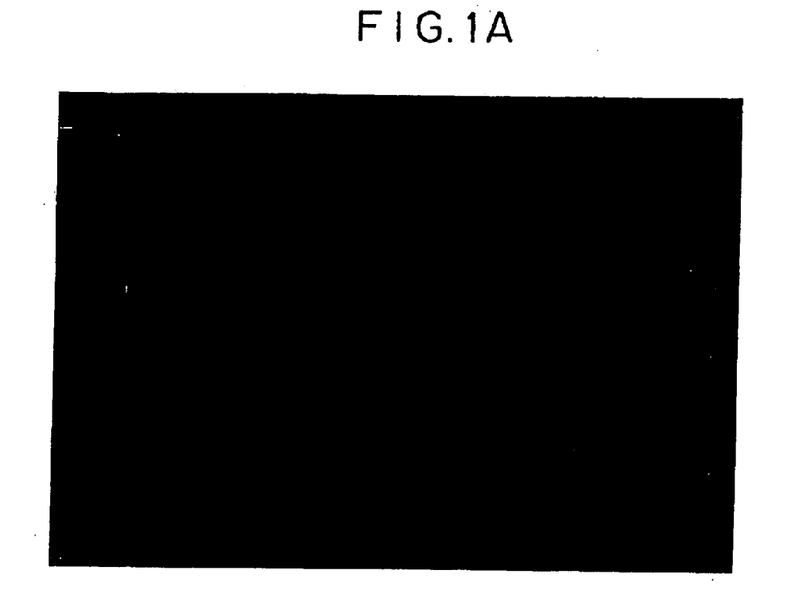
FIG. 1A shows reactivity of the antibody FARS-91 with the control spermatozoa (bright field; magnification of 100)
Figure 1B:
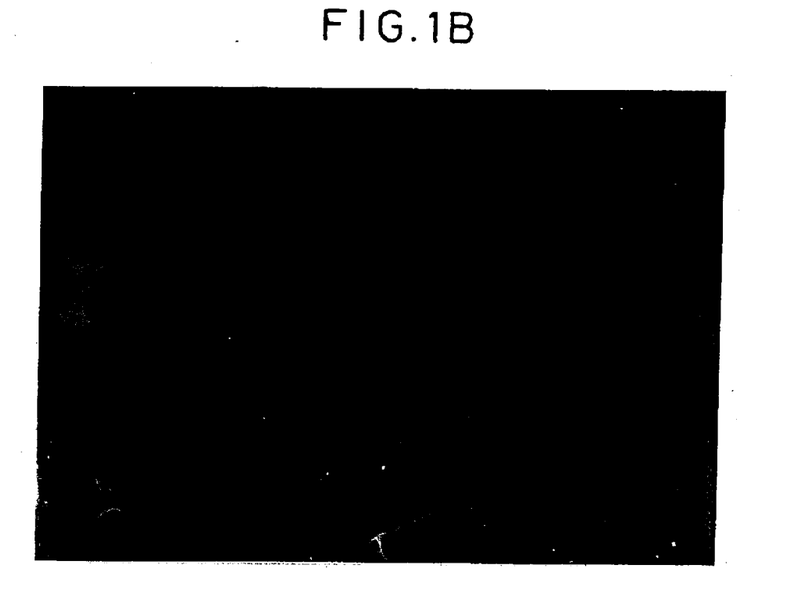
FIG. 1B shows reactivity of the antibody FARS-91 with the control spermatozoa (FITC excitation; magnification of 100)
Figure 2A:
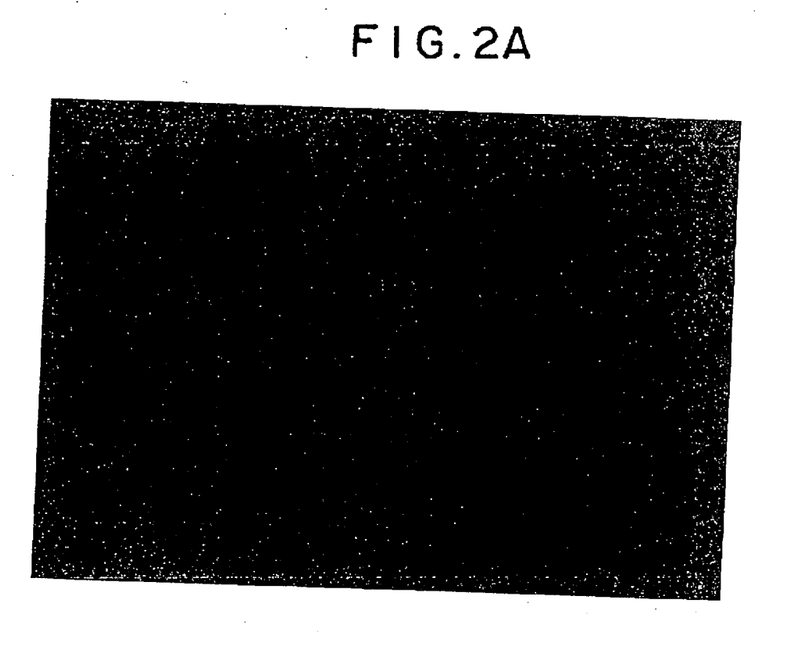
FIG. 2A shows reactivity of the antibody FARS91 with spermatozoa treated with A23187 (bright field; magnification of 100)
Figure 2B:
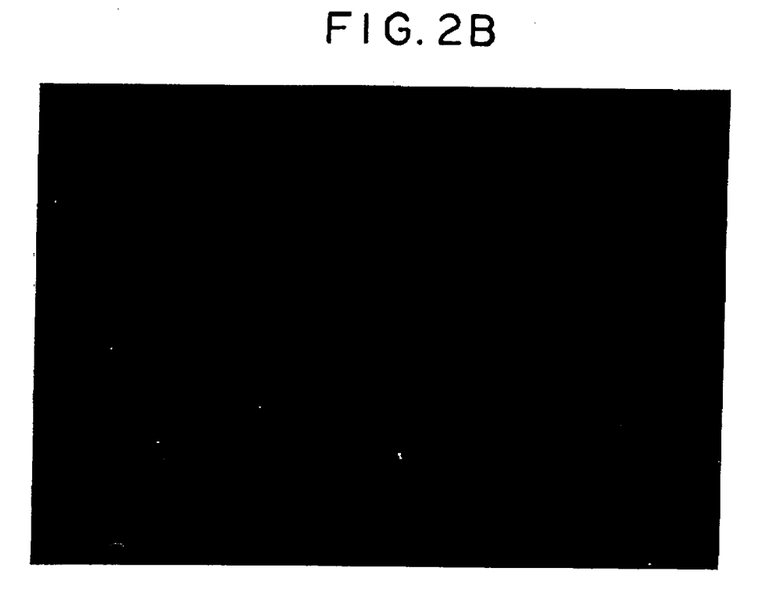
FIG. 2B shows reactivity of the antibody FARS-91 with spermatozoa treated with A23187 (FITC excitation; magnification of 100)
Figure 3A:
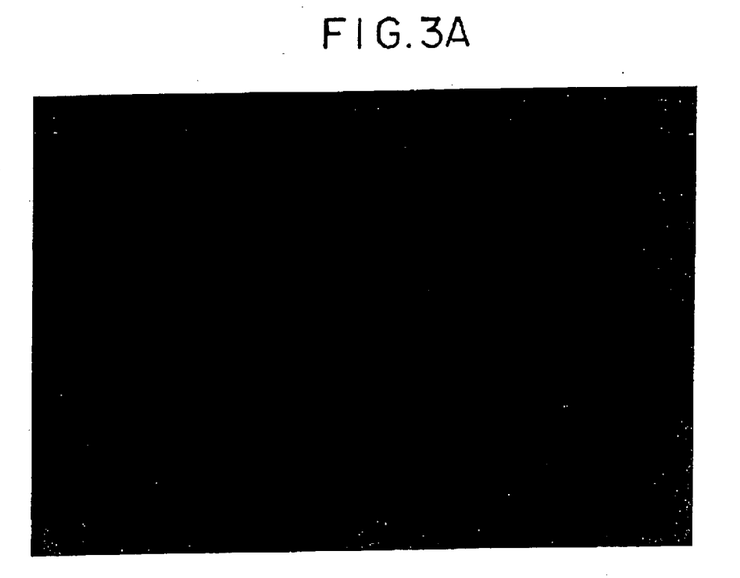
FIG. 3A shows reactivity of the antibody FARS-92 with the control spermatozoa (bright field; magnification of 100)
Figure 3B:
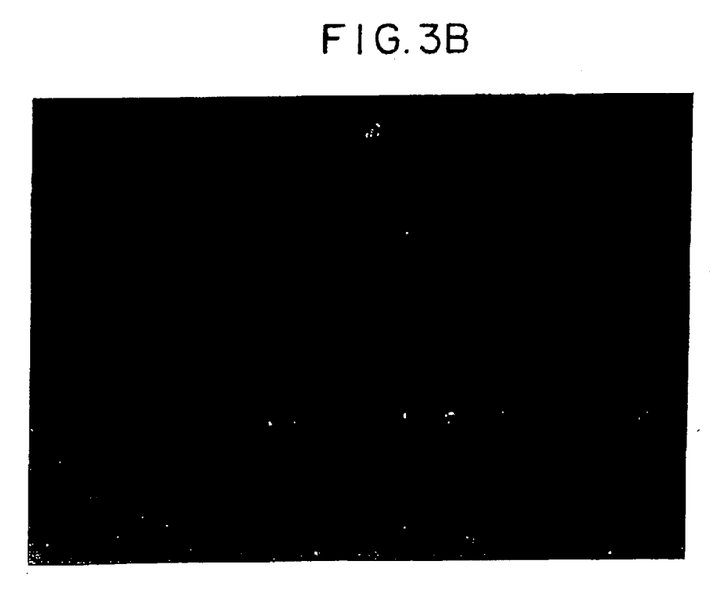
FIG. 3B shows reactivity of the antibody FARS92 with the control spermatozoa (FITC excitation; magnification of 100)
Figure 4A:
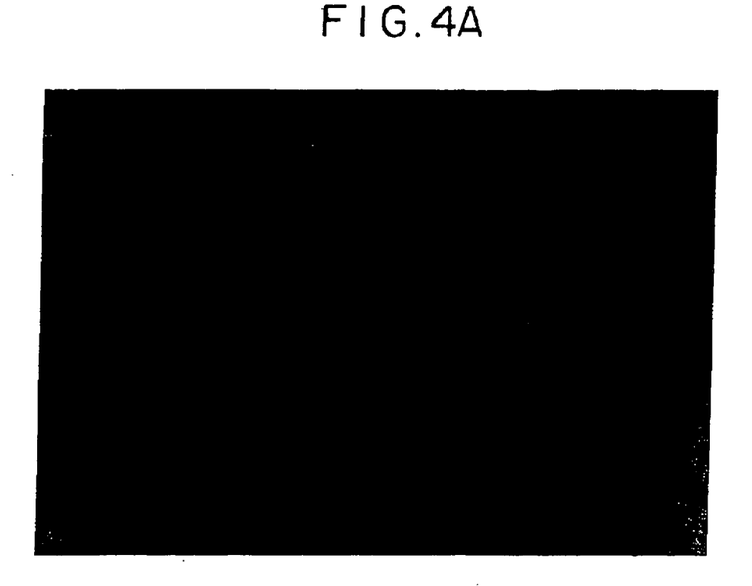
FIG. 4A shows reactivity of the antibody FARS-92 with spermatozoa treated with A23187 (bright field; magnification of 100)
Figure 4B:
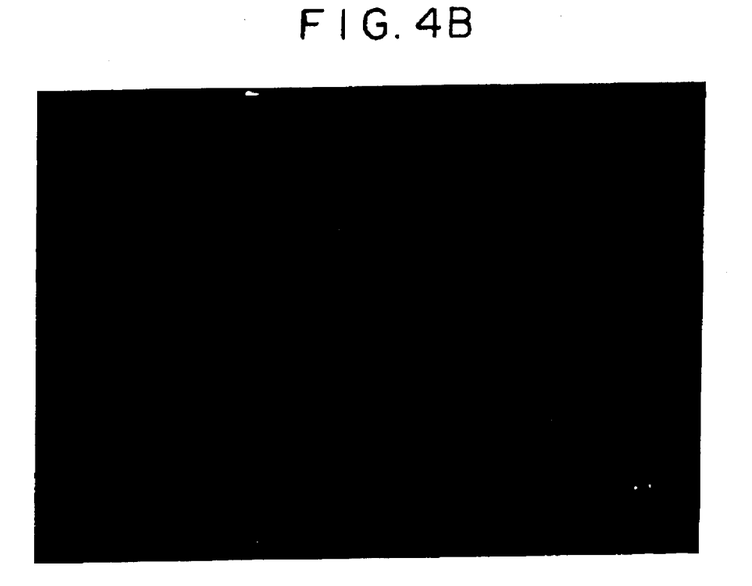
FIG. 4B shows reactivity of the antibody FARS-92 with spermatozoa treated with A23187 (FITC excitation; magnification of 100)

As a result, it was found that 65.5±3.7% of spermatozoa treated with A23187 (FIGS. 2A and B) reacted with FARS-91 antibody (in control spermatozoa (FIGS. 1A and B), 12.5±3.1%), while 59.8±3.8% of spermatozoa treated with A23187 (FIGS. 4A and B) reacted with FARS-92 antibody (in control spermatozoa (FIGS. 3A and B), 8.5+1.7%). From these results, it was confirmed that the FARS-91 antibody and the FARS-92 antibody react specifically with spermatozoa in which the acrosome reaction has occurred.

Example 9

Observation of Frozen-Thawed Spermatozoa by a FITC-PSA Staining Method

It has been said that freezing and thawing of spermatozoa physically destroys the plasma membrane and/or acrosomal outer membrane and leads to a state which follows the occurrence of the acrosome reaction (hereinafter, referred to as pseudo-acrosome reaction). Therefore, using the fluorescent pigment FITC-PSA which has specificity to the contents of acrosomal granules present in the acrosome before the acrosome reaction, it was confirmed whether frozen-thawed spermatozoa cause the pseudo-acrosome reaction. In general, in spermatozoa in which no acrosome reaction occurs, fluorescence is observed at the sperm head since the fluorescent pigment FITC-PSA is bound to the contents of acrosomal granules in the acrosome.

Smears of fresh spermatozoa and frozen-thawed spermatozoa were prepared, allowed to stand at room temperature for 2 hours or longer to dry, fixed in 95% methanol for 2 hours, and washed 3 times by immersion in distilled water for every 10 minutes. After washing, the smears were allowed to react with a FITC-PSA (50 mg/mL) solution at room temperature under shading for 3 hours. After washing with distilled water, the smears were observed under a fluorescence microscope. Spermatozoa exhibiting fluorescence on their head were judged positive.

Figure 5A:
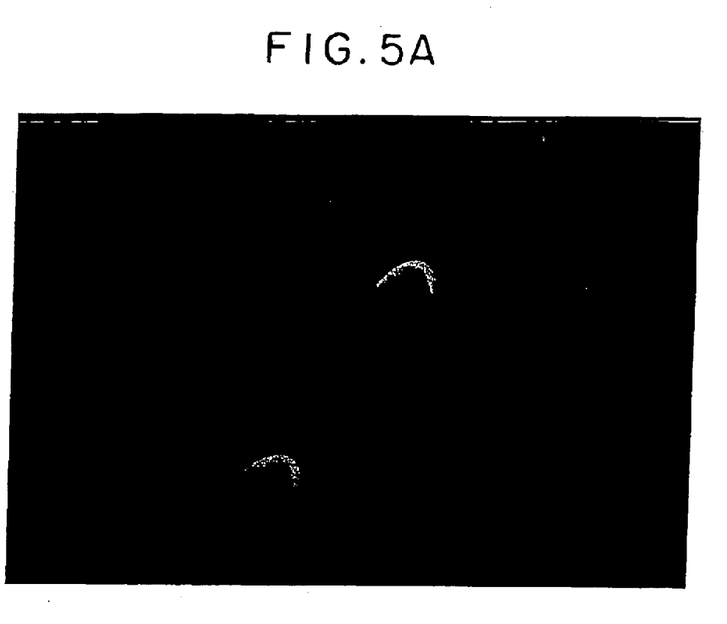
FIG. 5A shows fresh spermatozoa (positive; magnification of 400)
Figure 5B:
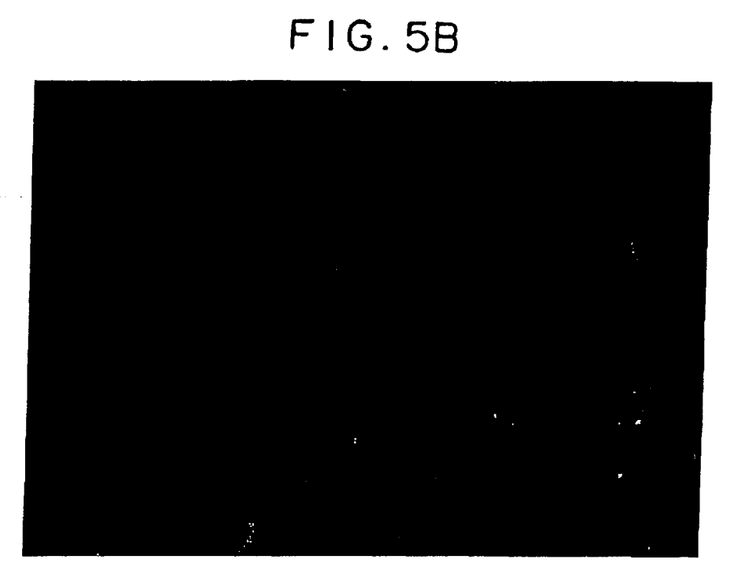
FIG. 5B shows frozen and thawed spermatozoa (negative; magnification of 400)

Fluorescence was observed on the head of fresh spermatozoa (FIG. 5A), while almost no fluorescence was observed on that of frozen-thawed spermatozoa (FIG. 5B).

That is, it was confirmed that fresh spermatozoa cause no acrosome reaction, but in frozen-thawed spermatozoa a pseudo-acromal reaction does occur.

Example 10

Reactivity of FARS-91 and FARS-92 Antibodies to Frozen-Thawed Spermatozoa

Since it was proven in Example 9 that a pseudo-acromal reaction occurs in frozen-thawed spermatozoa, it was examined whether FARS-91 and FARS-92 antibodies react specifically with spermatozoa that cause the pseudo-acrosome reaction, i.e., frozen-thawed spermatozoa.

To 30 μL of fresh spermatozoa or frozen-thawed spermatozoa $1\times10^6$/mL), 50 μL of ascites fluid containing FARS-91 antibody or FARS-92 antibody was added. The mixture was gently stirred, allowed to react at 37° C. for 30 minutes, and washed with 0.4% BSA-containing TYH culture broth by centrifugation (37° C., 2800 rpm, 5 min). After washing, 30 μL of 400-fold diluted FITC-labeled anti-mouse IgG was added and allowed to react at 37° C. for 1 hour. The mixture was washed twice with 0.02% $NaN_3$-containing PBS(−) by centrifugation (room temperature, 2800 rpm, 5 min) and observed under a fluorescence microscope.

Figure 6A:
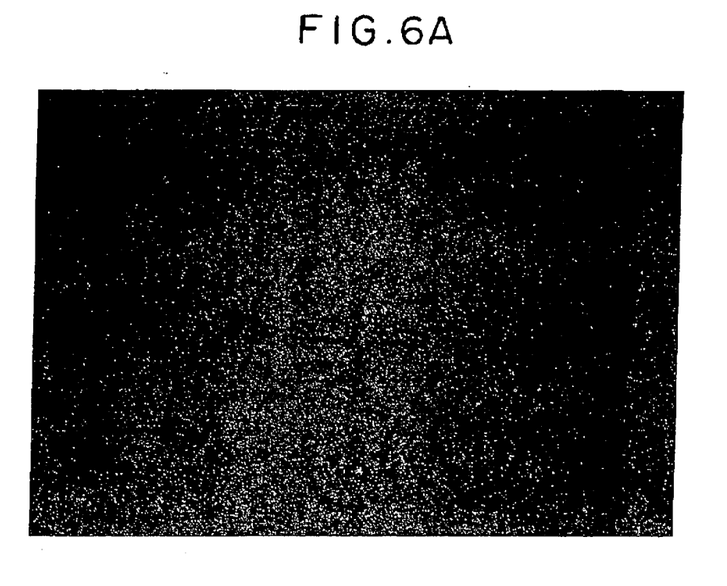
FIG. 6A shows reactivity of the antibody FARS-91 with fresh spermatozoa (negative; magnification of 200)
Figure 6B:
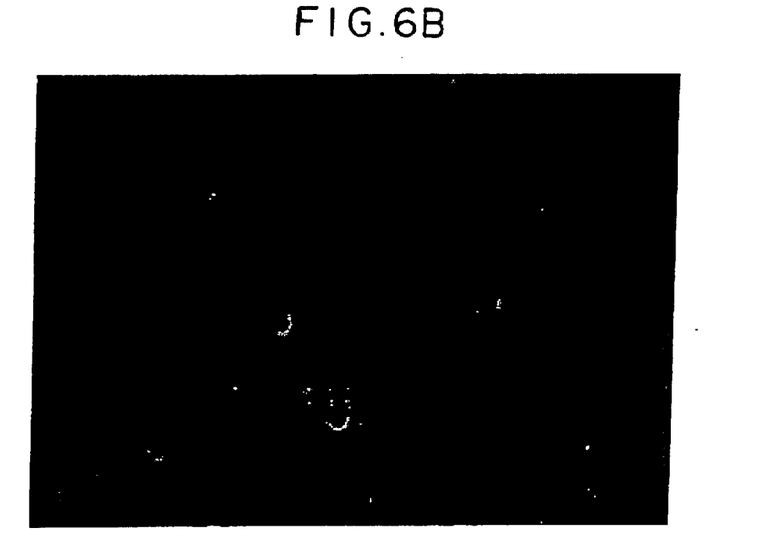
FIG. 6B shows reactivity of the antibody FARS-91 with the frozen and thawed spermatozoa (positive; magnification of 200)
Figure 7A:
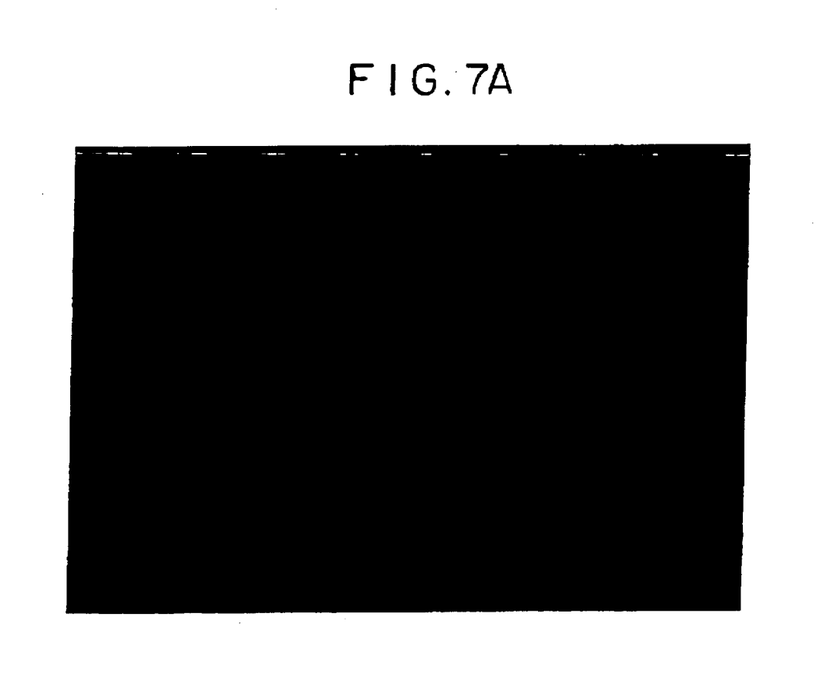
FIG. 7A shows reactivity of the antibody FARS-92 with fresh spermatozoa (negative; magnification of 200)
Figure 7B:
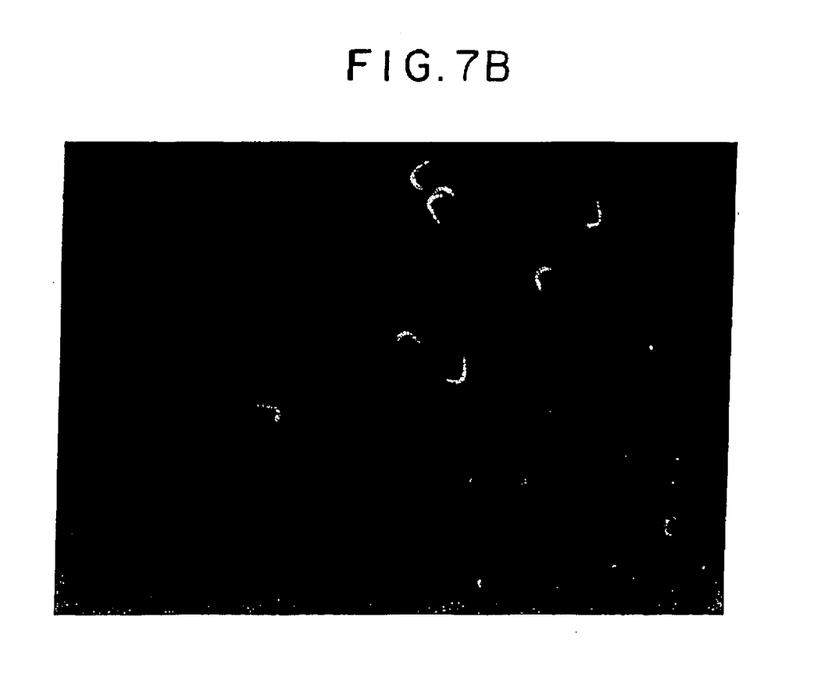
FIG. 7B shows reactivity of the antibody FARS-92 with the frozen and thawed spermatozoa (positive; magnification of 200)

As a result, fluorescence was observed at the head of most of the frozen-thawed spermatozoa for both of the FARS-91 and FARS-92 antibodies (FIG. 6B and FIG. 7B), while the rate of fluorescent spermatozoa was greatly reduced in fresh spermatozoa (FIG. 6A and FIG. 7A). According to Examples 9 and 10, it was confirmed that the FARS-91 and FARS-92 antibodies also react specifically with spermatozoa which cause a pseudo-acrosome reaction.

Example 11

Reactivity of FARS-91 and FARS-92 Antibodies to Spermatozoa which Have Been Frozen and Thawed After Treatment with A23187

Reactivity of the FARS-91 and FARS-92 antibodies was examined for spermatozoa which have been frozen and thawed after treatment with A23187 to cause chemical and physical acrosome reactions.

Spermatozoa collected from the cauda epididymis of Jcl:SD male rats were prepared to $1\times10^6$/mL with 0.4% BSA-containing TYH culture broth. A23187 dissolved in DMSO was added to a final concentration of 2 μM, and the mixture was allowed to react at 37° C. for 20 minutes. After the reaction was complete, the treated spermatozoa were washed twice with PBS(−), prepared to a predetermined concentration, and frozen at −20° C. After thawing, the ascites fluid containing FARS-91 antibody or FARS-92 antibody was added, and allowed to react at 37° C. for 30 minutes. The mixture was washed twice with 0.4% BSA-containing TYH culture broth by centrifugation (37° C., 2800 rpm, 5 min), 30 μL of FITC-labeled anti-mouse IgG was added, and allowed to react at 37° C. for 60 minutes. The mixture was washed twice with 0.02% $NaN_3$-containing PBS(−) by centrifugation (room temperature, 2800 rpm, 5 min), and observed under a fluorescence microscope.

Figure 8A:
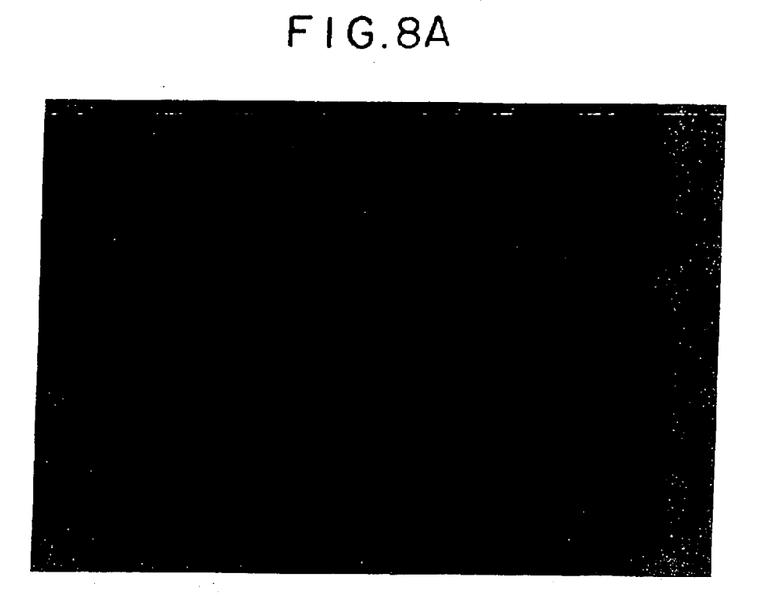
FIG. 8A shows reactivity of the antibody FARS-91 with the frozen and thawed spermatozoa after treatment with A23187 (bright field; magnification of 100)
Figure 8B:
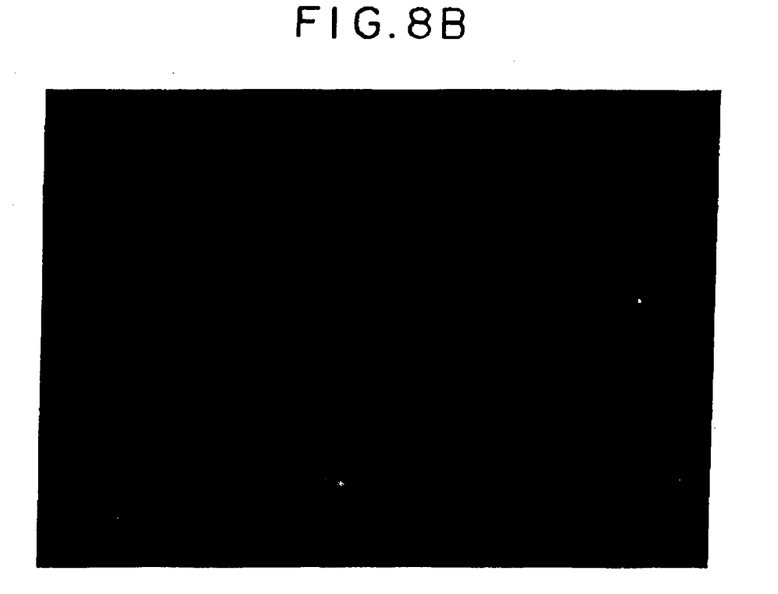
FIG. 8B shows reactivity of the antibody FARS-91 with the frozen and thawed spermatozoa after treatment with A23187 (FITC excitation; magnification of 100)
Figure 9A:
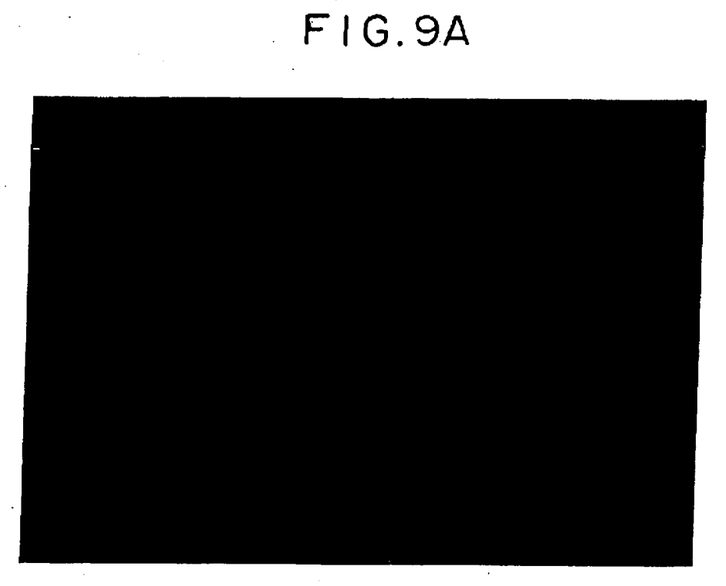
FIG. 9A shows reactivity of the antibody FARS-92 with the frozen and thawed spermatozoa after treatment with A23187 (bright field; magnification of 100)
Figure 9B:
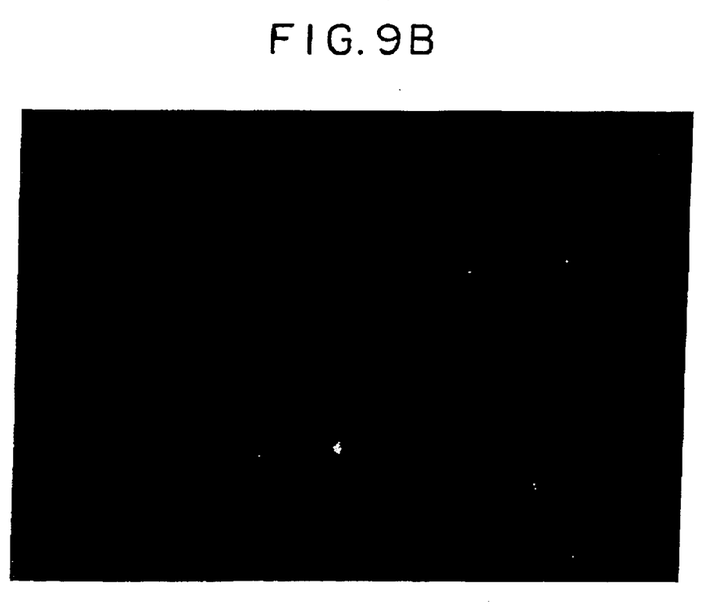
FIG. 9B shows reactivity of the antibody FARS-92 with the frozen and thawed spermatozoa after treatment with A23187 (FITC excitation; magnification of 100).

As a result, fluorescence was observed on the head of nearly 100% of spermatozoa which have been frozen-thawed after treatment with A23187 in the FARS-91 (FIGS. 8A and B) and FARS-92 (FIGS. 9A and B) antibodies.

Example 12

Reactivity of FARS-91 and FARS-92 Antibodies to Human Frozen-Thawed Spermatozoa

It was examined by an indirect fluorescence antibody method whether or not the FARS-91 and FARS-92 antibodies react to human frozen-thawed spermatozoa.

To 30 μL of human frozen and thawed spermatozoa $1\times10^6$/mL), 50 μL of ascites fluid containing FARS-91 antibody or FARS-92 antibody was added. The mixture is allowed to react at 37° C. for 30 minutes, and washed twice with 0.02% $NaN_3$-containing PBS(−) by centrifugation (37° C., 2800 rpm, 5 min). Then, 30 μL of 400-fold diluted FITC-labeled anti-mouse IgG was added and allowed to react at 37° C. for 1 hour. The mixture was washed in the same manner and observed under a fluorescence microscope.

Figure 10A:
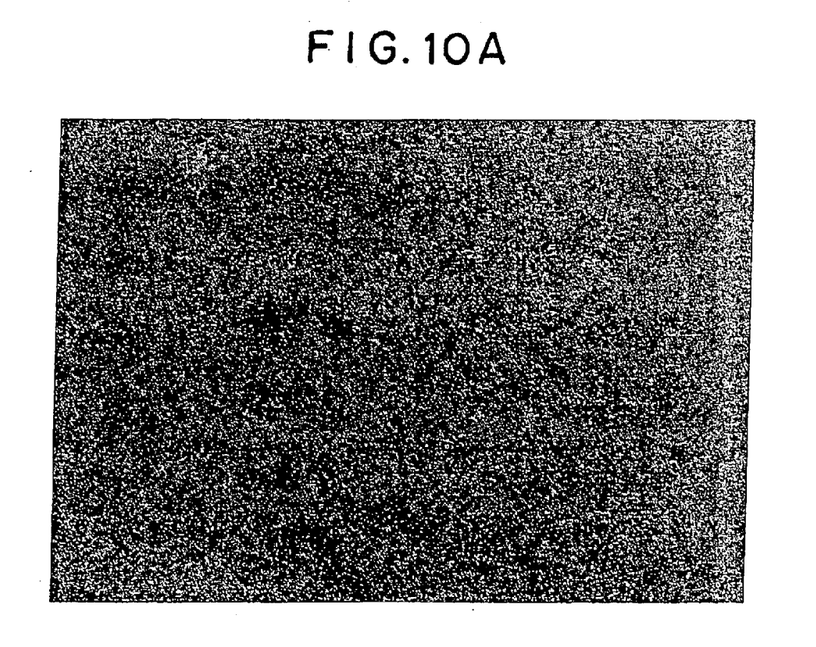
FIG. 10A shows reactivity of the antibody FARS-91 with the frozen and thawed human spermatozoa (FITC excitation; magnification of 200)
Figure 10B:
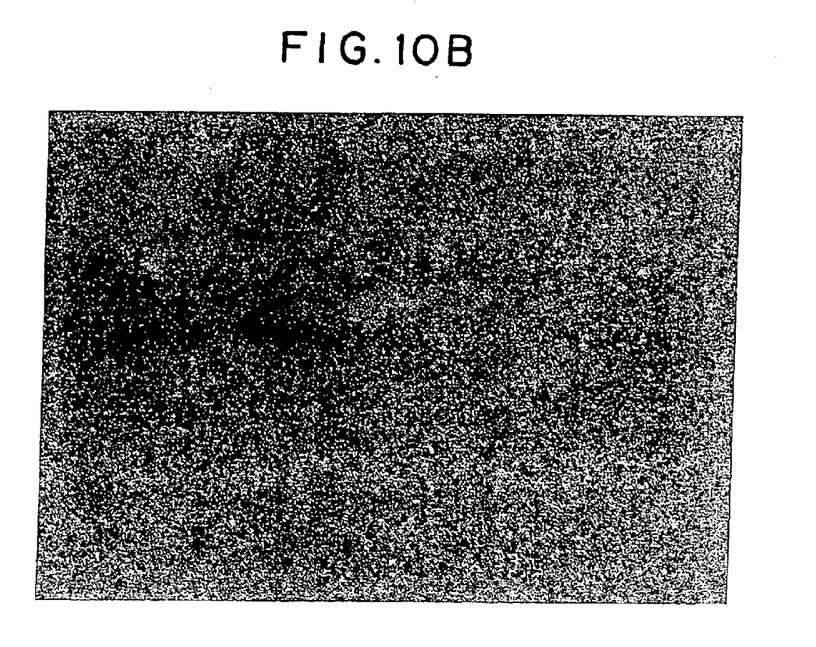
FIG. 10B shows reactivity of the antibody FARS-92 with the frozen and thawed human spermatozoa (FITC excitation; magnification of 200)

Both of the FARS-91 (FIG. 10A) and FARS-92 (FIG. 10B) antibodies did not emit fluorescence in reaction with human frozen and thawed spermatozoa. Thus, it was shown that these antibodies are not bound to human frozen and thawed spermatozoa.

Example 13

Preparation of a Kit for Characterization of Fertility

A suspension of Dynabeads M-450 sheep anti-mouse IgG (FC) was well shaken, and a necessary amount was placed on tubes for centrifugation in a clean bench and subjected to centrifugation at 4° C. and 2000 rpm for 5 minutes. After removal of the supernatant, a non-specific adsorption blocker, Block Ace (Snow Brand), was added in an amount equal to the collected Dynabeads, and the mixture was incubated under shaking at 37° C. for 1 hour. After termination of incubation, the mixture was centrifuged at 4° C. and 2000 rpm for 5 minutes to remove the supernatant. Sterilized PBS(−) at twice the amount of the collected Dynabeads was added, and the mixture was stirred and centrifuged at 4° C. and 2000 rpm for 5 minutes to remove the supernatant. This operation was further repeated twice to completely remove the non-specific adsorption blocker. Finally, PBS(−) in an amount equal to the collected Dynbeads was added to the precipitate, and then the ascites liquid containing the FARS-91 antibody or FARS-92 antibody was added. The mixture was mixed well and allowed to react under shaking at 37° C. for 1 hour. Because dispersion of beads was insufficient under shaking due to their heavy specific gravity, the mixture was frequently stirred well using a mixer during the reaction. After the reaction was complete, the mixture was centrifuged at 4° C. and 2000 rpm for 5 minutes to remove the supernatant. Then, the sterilized PBS(−), in an twice amount of the collected Dynbeads, was added to the precipitate. After mixing well, the mixture was centrifuged at 4° C. and 2000 rpm for 5 minutes to remove the supernatant. This washing operation was repeated 3 more times to completely remove the FARS-91 or FARS-92 antibody that remain unchanged. Finally, PBS(−) containing 0.02% $NaN_3$ and 2% bovine serum albumin(BSA) in an amount that is 10 times the amount of the collected Dynabeads was added to the precipitate obtained. This bead suspension was mixed well, of which 20 μL was dispensed into microtubes, and to which microtubes 380 μL of 2% BSA-containing PBS(−) was added. The number of beads was prepared to be $0.5 \times 10^6$/mL by counting on a Thoma's hemocytometer. On the other hand, spermatozoa collected from the cauda epididymis of Jcl:SD male rats were prepared to be $1 \times 10^6$/mL with 0.4% BSA-containing TYH culture broth. To 10 μL of antibody-binding beads at $0.5 \times 10^6$/mL, 100 μL of fresh rat spermatozoa prepared to $1 \times 10^6$/mL was added, and the mixture was allowed to react at 37° C. under 5% $CO_2$.

For both the FARS-91 and FARS-92 antibodies, the aggregation of the beads was not observed immediately after addition of rat spermatozoa, but it was recognized after a lapse of 6 hours.

Example 14 (Kit)

By combining the following components, a kit was prepared:
TYH solution containing no sodium hydrogen carbonate and bovine serum albumin;
7% Sodium hydrogen carbonate;
Bovine serum albumin; and
FARS-91 beads or FARS-92 beads.

INDUSTRIAL APPLICABILITY

The present invention provides monoclonal antibodies reacting specifically to rat acrosome reacted sperm. Additionally, the invention provides a kit for evaluation of fertility using said antibodies, by which fertility can be conveniently evaluated within a short period of time without requiring skillful technique or troublesome operations.

What is claimed is:

1. A hybridoma deposited under accession number FERM BP-7401.

2. A hybridoma deposited under accession number FERM BP-7402.

3. A monoclonal antibody specifically reacting to rat acrosome reacted sperm, said monoclonal antibody provided by a hybridoma deposited under accession number FERM BP-7401.

4. A method for evaluating fertility of rat spermatozoa, comprising:
   a) contacting rat spermatozoa to be evaluated with the antibody of claim 3, wherein said antibody is labeled; and
   b) detecting an amount of label attached to the spermatozoa and evaluating the fertility of rat spermatozoa.

5. A composition for measuring fertility of rat spermatozoa, comprising the antibody of claim 3.

6. A composition for measuring fertility of rat spermatozoa, comprising beads carrying the antibody of claim 3.

7. A monoclonal antibody specifically reacting to rat acrosome reacted sperm, said monoclonal antibody produced by a hybridoma deposited under accession number FERM BP-7402.

8. A method for evaluating fertility of rat spermatozoa, comprising:
   a) contacting rat spermatozoa to be evaluated with the antibody of claim 7, wherein said antibody is labeled; and
   b) detecting an amount of label attached to the spermatozoa and evaluating the fertility of rat spermatozoa.

9. A composition for measuring fertility of rat spermatozoa, comprising the antibody of claim 7.

10. A composition for measuring fertility of rat spermatozoa, comprising beads carrying the antibody of claim 7.

11. A kit for evaluating fertility, comprising the antibody of claim 3 or claim 7.

12. A kit for evaluating fertility, comprising the composition of any one of claims 5, 6, 9, and 10.

* * * * *